(12) United States Patent
Varrichio

(10) Patent No.: US 7,484,129 B1
(45) Date of Patent: Jan. 27, 2009

(54) PHYSIOLOGIC EVENT MONITORING DEVICE HAVING ROBUST INTERNAL CONTROL

(75) Inventor: Anthony J. Varrichio, Plano, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 565 days.

(21) Appl. No.: 11/208,023

(22) Filed: Aug. 19, 2005

Related U.S. Application Data

(60) Provisional application No. 60/603,474, filed on Aug. 20, 2004, provisional application No. 60/603,529, filed on Aug. 20, 2004.

(51) Int. Cl.
- *A61B 5/04* (2006.01)
- *A61B 5/0402* (2006.01)
- *A61B 5/0432* (2006.01)

(52) U.S. Cl. .................. 714/42; 714/718; 714/721; 714/723; 365/201; 365/226; 365/227; 600/508; 600/509; 600/515; 600/517; 600/527

(58) Field of Classification Search .................. 600/508, 600/509, 515, 517, 527; 714/42, 718, 721, 714/723
See application file for complete search history.

(56) References Cited

U.S. PATENT DOCUMENTS

| | | | |
|---|---|---|---|
| 5,944,745 A * | 8/1999 | Rueter | 607/27 |
| 5,987,352 A | 11/1999 | Klein et al. | |
| 6,236,882 B1 | 5/2001 | Lee et al. | |
| 6,412,490 B1 | 7/2002 | Lee | |
| 6,526,314 B1 * | 2/2003 | Eberle et al. | 600/523 |
| 6,684,100 B1 * | 1/2004 | Sweeney et al. | 600/517 |
| 7,130,678 B2 * | 10/2006 | Ritscher et al. | 600/523 |
| 2005/0090719 A1 * | 4/2005 | Scheiner et al. | 600/300 |

* cited by examiner

*Primary Examiner*—Carl H Layno
*Assistant Examiner*—Yun Haeng Lee
(74) *Attorney, Agent, or Firm*—Christopher S. L. Crawford; Peter Lando; Melissa Acosta

(57) ABSTRACT

Categories are established for use in physiological monitoring devices and these categories are prioritized such that data indicative of a critical event self-triggers a communication to an external receiver for the purpose of re-transmitting the critical data for use by a clinician. The categories can be established by the clinician and, if desired, the precise monitored data parameters can be assigned to specific categories. Far-field transmission can be used to send certain stored data to an external receiver, provision is made for externally charging the device batteries.

14 Claims, 4 Drawing Sheets

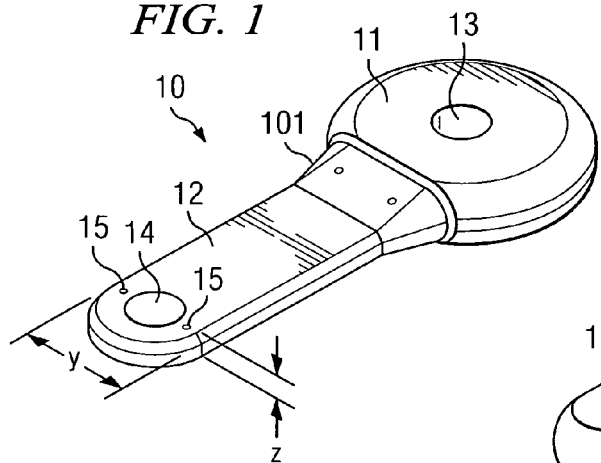
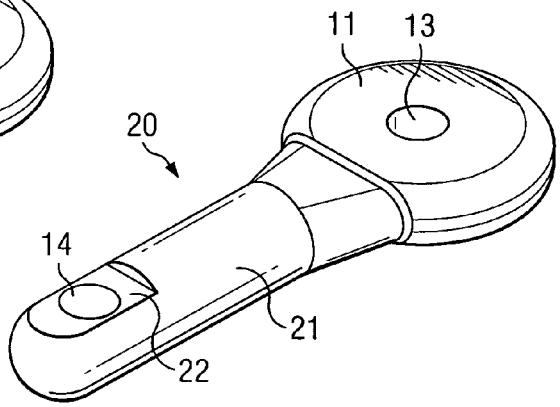
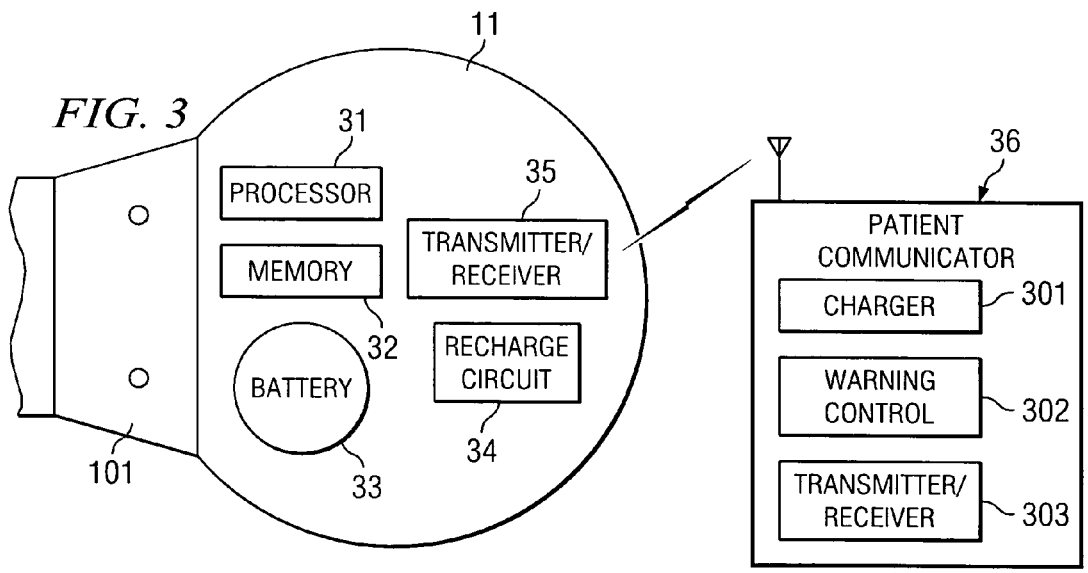
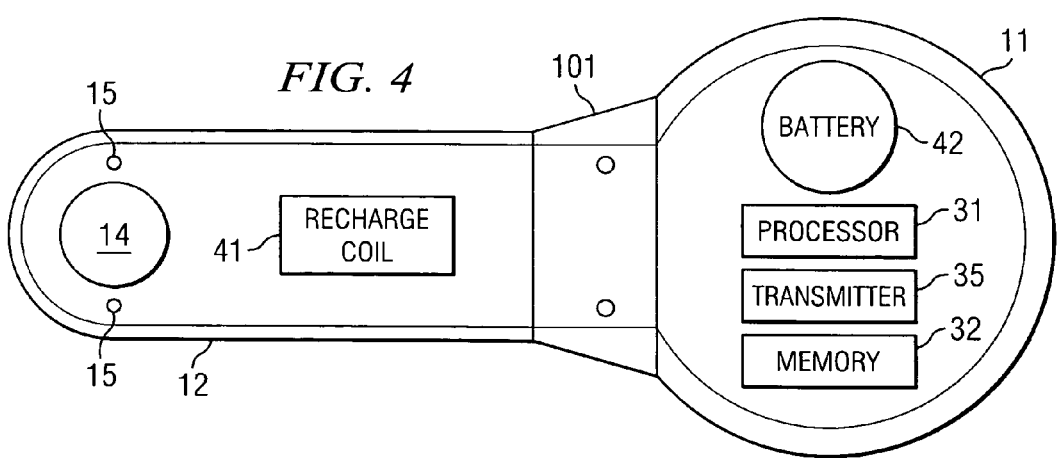

| CATEGORY | PRIORITY | TRIGGER VALUE |
|---|---|---|
| TACHYCARDIA | 2 | >X |
| BRADYCARDIA | 1 | <Y |
| ARRHYTHMIA | 2 | >Z SECONDS |
| FIBRILLATION | 1 | |
| SYNCOPY | 1 | # REPITITIONS |
| MISC 1 | 3 | |

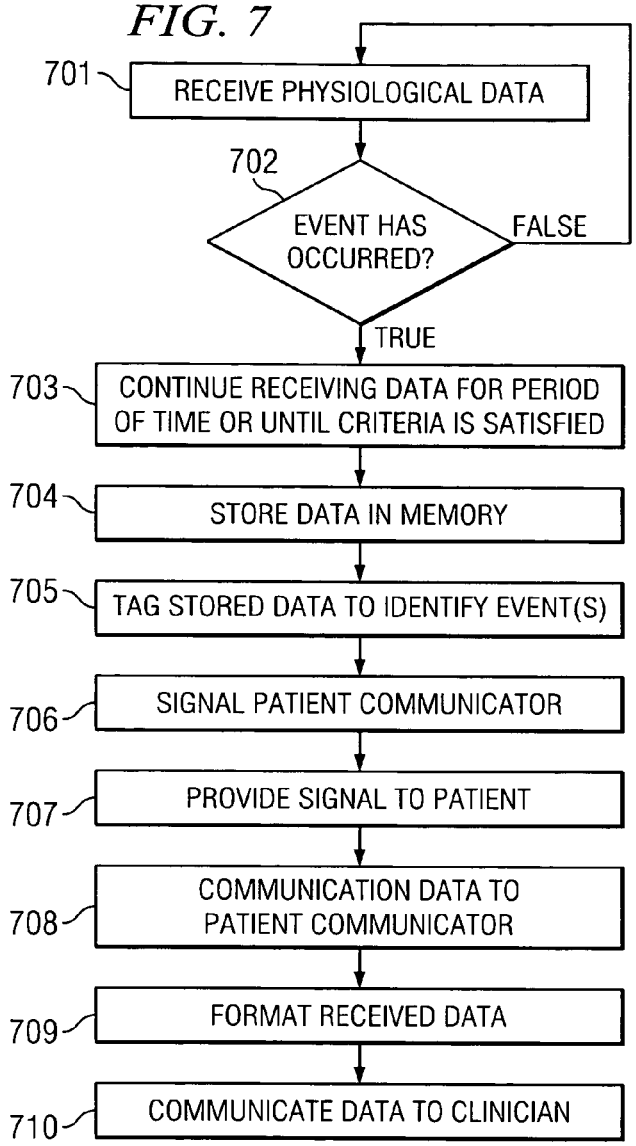
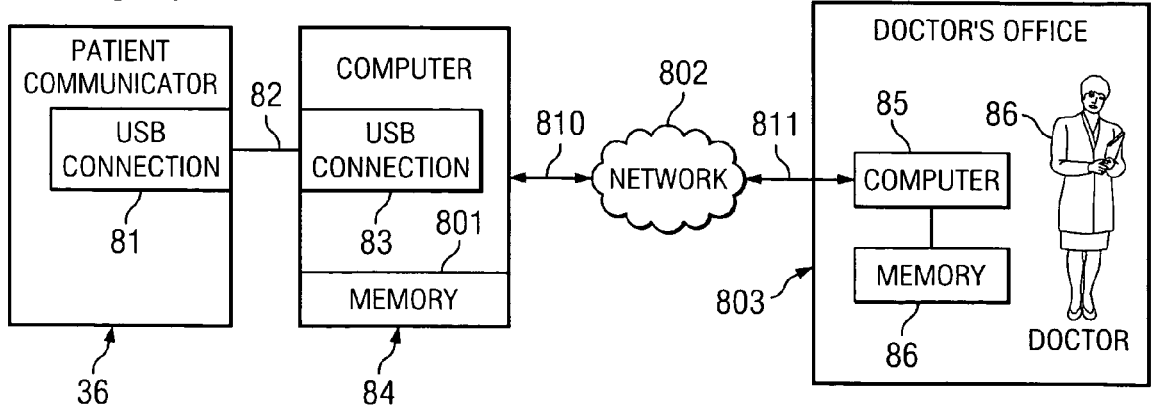

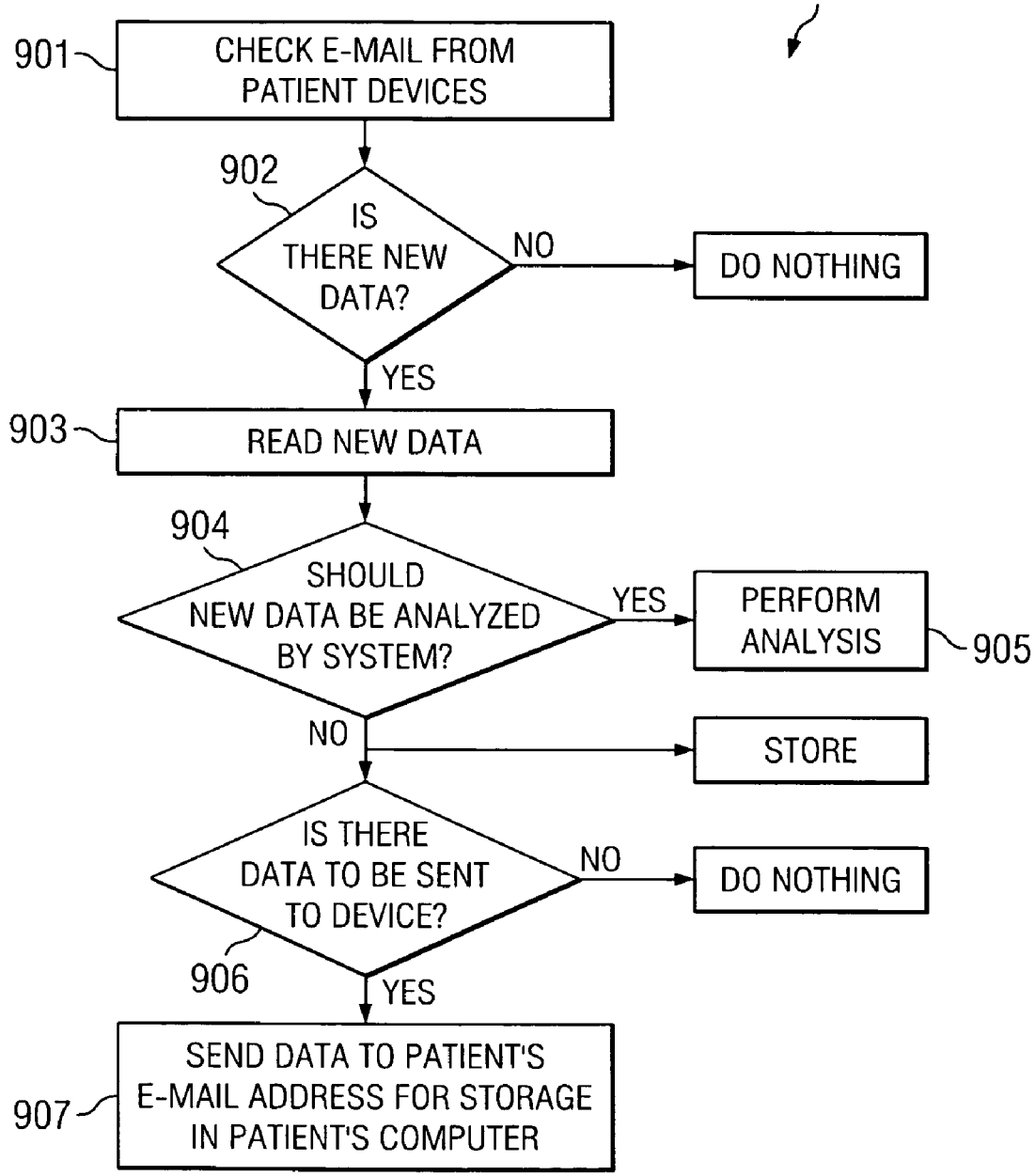

PHYSIOLOGIC EVENT MONITORING DEVICE HAVING ROBUST INTERNAL CONTROL

CROSS REFERENCE TO RELATED APPLICATIONS

The present application claims the benefit of U.S. Provisional Application Ser. No. 60/603,474, filed Aug. 20, 2004, entitled "PHYSIOLOGIC EVENT MONITORING DEVICE," and U.S. Provisional Application Ser. No. 60/603,529, filed Aug. 20, 2004, entitled "PHYSIOLOGIC EVENT MONITORING DEVICE HAVING ROBUST INTERNAL CONTROL," which are incorporated herein by reference.

TECHNICAL FIELD

The present application is generally related to implantable medical devices that monitor for events in patients.

BACKGROUND

A number of products exist for implantation within a patient with minimally invasive intrusion to monitor for one or several physiologic events. An example of such a device is described in U.S. Pat. No. 5,987,352 issued Nov. 16, 1999. The device shown in the above-described patent is enclosed within a rigid shell. The shell is somewhat cylindrical. One electrode is disposed at one end of the shell and another electrode is disposed on the other end of the shell. The two electrodes are used to measure an electrical waveform in the body (e.g., ECG signals). The waveform is sampled and the sampled data is stored within memory of the device. An external device can be positioned on the patient's body immediately above the monitoring device to enable the external device to retrieve the stored data for subsequent analysis by a clinician.

SUMMARY

One embodiment of the present invention is an implantable device for recording physiological waveforms, the device comprising an electronic circuitry for sampling a physiological waveform of a patient, a memory for storing physiological data, a processor under the control of executable instructions for processing samples of the physiological waveform, wherein the processor is operable (i) to detect a predefined event in the physiological waveform by analyzing the physiological waveform against multiple parameters with each of the multiple parameters applied to a different segment of the physiological waveform and (ii) to store physiological data in the memory in response to detection of the predefined event; and a wireless communication module for communicating with a device external to the patient after the implantable device has been implanted in the patient.

In some embodiments, multiple triggers are used to identify physiological data to be stored within the memory of a monitoring device. When the physiological data is stored, the particular trigger is identified by tagging the data with an appropriate identifier. By tagging or otherwise suitably identifying the trigger, some embodiments enable the stored data to be managed and/or analyzed in an efficient manner. Stored data can be prioritized according to a physician's requirements. If the stored data exceeds the memory capacity of the monitoring device, the monitoring device does not overwrite physiological data associated with higher priority triggers with physiological data associated with lower priority triggers. Additionally, even if the memory of the device is not exceeded, the tagging functionality of the monitoring device enables the most relevant data to be retrieved and reviewed by a clinician in an efficient manner, i.e., the clinician can identify and retrieve data pertaining to one or several specific triggers. In some embodiments, the trigger functionality can be controlled by the clinician in a more accurate manner by utilizing "signature references." Multiple signature references can also be applied to physiological data. The reference signatures can be applied in combination with one or several conventional static trigger criteria. In some embodiments, the signature references are applied in a time dependent manner. For example, a subset of signature references could be employed during daytime hours and another subset of signature references could be employed during nighttime hours.

In some embodiments, the monitoring device includes a self-diagnostic software module that analyzes the memory of the monitoring device used to store the physiological data. Specifically, the software module can write known values to memory locations in the memory and retrieve the known values from the memory locations. When the retrieved values deviate from the expected values, defective memory locations can be identified. In addition, other types of memory defects can be identified. For example, certain memory defects can cause writing to and/or reading from a particular memory location to consume an undue amount of current and thereby more readily deplete battery power. Accordingly, some embodiments monitor the amount of current associated with each write/read transaction to detect such memory defects. By maintaining a table of defective memory locations, the monitoring device can avoid using such locations to maintain the integrity of the physiological data and to maintain the battery capacity of the device. In other embodiments, a suitable error correction code (ECC) scheme (e.g., a Reed-Solomon code correction algorithm) is additionally applied to the physiological data to maintain the integrity of the physiological data In some embodiments, the monitoring device operates in conjunction with an external patient communicator device. The patient communicator device can be kept on the person of the patient (on a belt, in a pocket, etc.). When an event of interest is detected and recorded by the monitoring device, the monitoring device signals the patient communicator device using far field wireless communication. The signal causes the patient communicator device to alert the patient. The patient can then take suitable action (e.g., seek suitable medical attention, allow the stored data to be communicated to an appropriate medical professional, etc.). The patient communicator device can also be used to communicate suitable parameters (e.g., signature references, priority information, etc.) to the monitoring device to control the operations of the monitoring device. The patient communicator device can also obtain status information from the monitoring device such as battery status, remaining memory capacity, detected event types, and/or the like. The patient communicator device can be implemented to perform other functions. For example, the patient communicator can include a USB port or other suitable interface to connect to digital devices to facilitate the communication of the stored physiological data to appropriate medical personnel. The USB port can also be used to charge the patient communicator device. Additionally, the patient communicator device can include a suitable coil to radiate RF power to the monitoring device to recharge the monitoring device.

The foregoing has outlined rather broadly the features and technical advantages of some embodiments in order that the detailed description that follows may be better understood.

Additional features and advantages will be described hereinafter which form the subject of the claims of the invention. It should be appreciated that the conception and specific embodiments disclosed may be readily utilized as a basis for modifying or designing other structures for carrying out the same purposes of the present invention. It should also be realized that such equivalent constructions do not depart from the invention as set forth in the appended claims. The novel features, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 1 depicts one embodiment of a monitoring device having a circular-shaped housing and an elongated probe section.

FIG. 2 depicts an embodiment of the device of FIG. 1 where a substantial length of the probe section is tubular.

FIG. 3 depicts a top view of one embodiment of the housing of the device of FIG. 1 having the electronics contained therein.

FIG. 4 depicts a top view of an alternate embodiment of a monitoring device.

FIG. 7 depicts a flowchart involving receiving, processing, and communicating physiological data according to one embodiment.

FIG. 8 depicts a patient communicator device in communication with a remote site according to one representative embodiment.

FIG. 9 depicts a flowchart for communication of physiological data to a physician according to one representative embodiment.

DETAILED DESCRIPTION

Figures 5, 6:
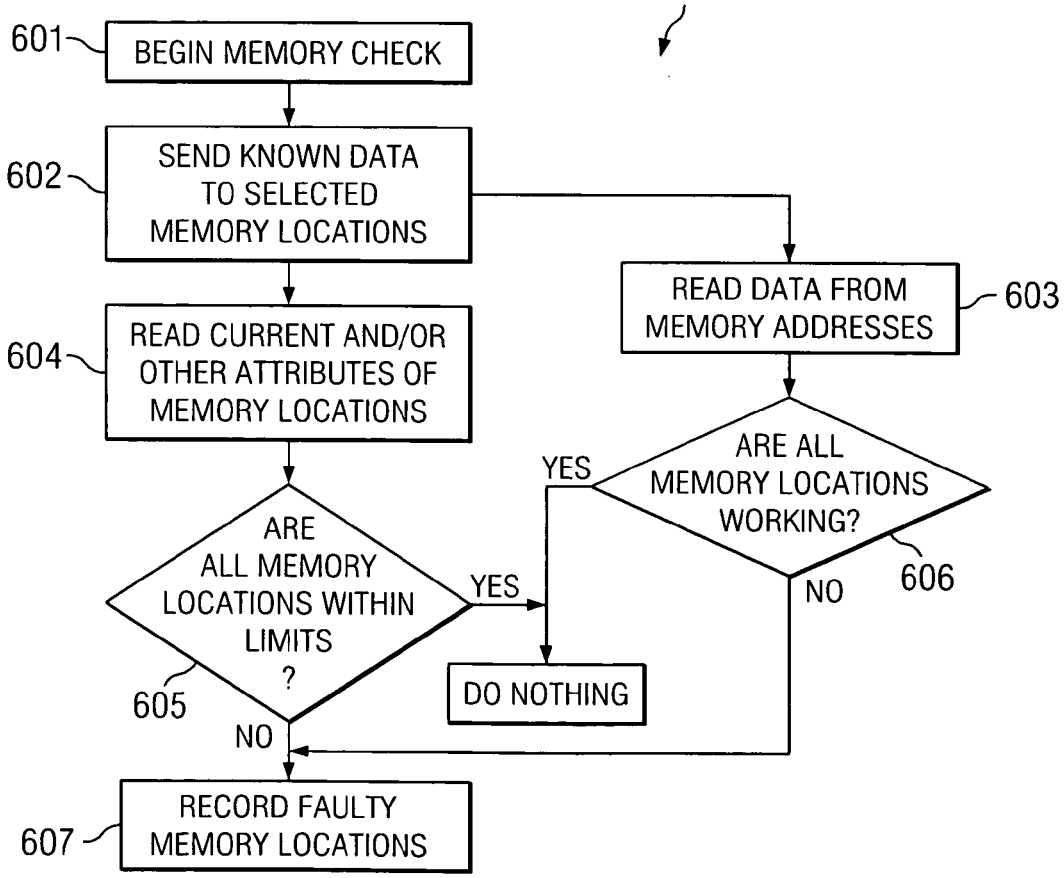
FIG. 5 depicts one embodiment of a table of event categories, category prioritizes, and trigger values according to one embodiment.
FIG. 6 depicts one embodiment of a flowchart for analyzing internal memory of a monitoring device according to one embodiment.

Implantable monitoring devices are currently used to monitor various physiological parameters in a patient. For example, the Reveal® product from Medtronic monitors a patient's cardiac activity over a period of time, collects information relating to a specific cardiac event, and transfers such information to a physician for evaluation. Such devices, however, can be used to monitor a wide range of medical conditions such as diabetes, respiratory function, kidney function, brain function and most other medical or physiological conditions.

These implantable monitoring systems balance size and functionality. Because the systems are implanted and used for diagnostic purposes, the devices should be small enough to be subcutaneously implanted (perhaps during a visit to a doctor's office or outpatient visit) and provide long term monitoring capabilities to ensure that the necessary medical events for diagnosis are captured and recorded. Certain embodiments of the present invention provide of a design that allows it to balance its small size with increased diagnostic monitoring and recording capabilities, providing physicians with greater information.

Although existing implantable monitoring devices can monitor physiologic events in some circumstances, existing monitoring devices are limited in a number of respects. For example, existing monitoring devices merely store physiologic data when a very simple "trigger" event occurs, i.e., heart rate exceeding a specified level. However, the use of such rudimentary criteria can omit detection of important physiologic events and can misidentify normal events. Additionally, failed memory elements within the monitoring devices can cause the stored physiological data to substantially reduce the value of the retrieved data for analysis by a clinician. Furthermore, the amount of data associated with multiple trigger events can exceed the memory capacity of known devices. Accordingly, previously stored data can be overwritten by data associated with a more recent trigger event in existing monitoring devices. However, the overwritten data can be of significantly greater relevance than the data associated with the more recent trigger event.

Prior art implantable monitoring devices are described in U.S. patent application Ser. No. 08/678,219, which has issued as U.S. Pat. No. 5,987,352 and its progeny. These devices are otherwise known to those in the art as implantable loop recorders or ILRs. An example of an ILR is the Reveal® Plus, sold by Medtronic. These devices are small and placed subcutaneously above the heart in the left chest area. Such devices are relatively simple in that they monitor cardiac activity for only one specific anomaly. Once the device recognizes the anomaly, the monitor will record the cardiac event correlating to the anomaly using a "loop recording" design.

In some embodiments of the present invention, multiple triggers are used to cause physiological data to be stored within the memory of a monitoring device. When the physiological data is stored, the particular trigger is identified by tagging the data with an appropriate identifier. By tagging or otherwise suitably identifying the trigger, some embodiments enable the stored data to be managed and/or analyzed in an efficient manner. For example, according to some embodiments, programmable prioritization parameters are used by the monitoring device to allocate memory for the various categories of physiological data. Specifically, a clinician may believe that a particular trigger is especially relevant to the observed symptoms of the patient. The clinician can use the parameters to indicate that the particular trigger possesses the highest priority. After the parameters are set in this manner, if the stored data exceeds the memory capacity of the monitoring device, the monitoring device does not overwrite physiological data associated with higher priority triggers with physiological data associated with lower priority triggers. Additionally, even if the memory of the device is not exceeded, the tagging functionality of the monitoring device enables the most relevant data to be retrieved and reviewed by a clinician in an efficient manner, i.e., the clinician can identify and retrieve data pertaining to one or several specific triggers.

In some embodiments, the trigger functionality can be controlled by the clinician in a more accurate manner by utilizing "signature references." The signature references are multiple parameters that are indicative of physiologic waveform characteristics. In some embodiments, the signature references are multi-point reference targets with tolerable variations. The multi-point reference targets are compared against multiple points of the monitored waveform. If the physiological event deviates from one of the point targets by the corresponding variation parameter, the data associated with the physiological event is stored and preferably tagged. Multiple signature references can also be applied to physiological data. The reference signatures can be applied in combination with one or several conventional static trigger criteria. In some embodiments, the signature references are applied in a time dependent manner. For example, a subset of signature references could be employed during daytime hours and another subset of signature references could be employed during nighttime hours.

In some embodiments, the monitoring device includes a self-diagnostic software module that analyzes the memory of the monitoring device used to store the physiological data. Specifically, the software module can write known values to memory locations in the memory and retrieve the known values from the memory locations. When the retrieved values deviate from the expected values, defective memory locations can be identified. In addition, other types of memory defects can be identified. For example, certain memory defects can cause writing to and/or reading from a particular memory location to consume an undue amount of current and thereby more readily deplete battery power. Accordingly, some embodiments monitor the amount of current associated with each write/read transaction to detect such memory defects. By maintaining a table of defective memory locations, the monitoring device can avoid using such locations to maintain the integrity of the physiological data and to maintain the battery capacity of the device. In other embodiments, a suitable error correction code (ECC) scheme is additionally applied to the physiological data to maintain the integrity of the physiological data.

In some embodiments, the monitoring device operates in conjunction with an external patient communicator device. The patient communicator device can be kept on the person of the patient (on a belt, in a pocket, etc.). When an event of interest is detected and recorded by the monitoring device, the monitoring device signals the patient communicator device using far field wireless communication. The signal causes the patient communicator device to alert the patient. The patient can then take suitable action (e.g., seek suitable medical attention, allow the stored data to be communicated to an appropriate medical professional, etc.). The patient communicator device can also be used to communicate suitable parameters (e.g., signature references, priority information, etc.) to the monitoring device to control the operations of the monitoring device. The patient communicator device can also obtain status information from the monitoring device such as battery status, remaining memory capacity, detected event types, and/or the like. The patient communicator device can be implemented to perform other functions. For example, the patient communicator can include a USB port or other suitable interface to connect to digital devices to facilitate the communication of the stored physiological data to appropriate medical personnel. The USB port can also be used to charge the patient communicator device. Additionally, the patient communicator device can include a suitable coil to radiate RF power to the monitoring device to recharge the monitoring device.

FIG. 1 depicts an advantageous design for a monitoring device according to one representative embodiment. Although a specific advantageous design is shown in FIG. 1, some embodiments can be employed without regard to the exterior design of the monitoring device. As an alternative to the design shown in FIG. 1, some embodiments can be implemented using conventional designs such as disclosed in U.S. patent application Ser. No. 08/678,219 and its progeny and the design employed the REVEAL® and Reveal® Plus monitor products.

As shown in FIG. 1, device 10 includes housing 11 in which at least one sensor 13 is preferably positioned. Attached to housing 11 is probe 12 which has an elongated flat shape which, or as is seen in FIG. 2, could be tubular (21), with a circular cross-section along a substantial length thereof with a flat area, such as flat area 22 near the distal end.

In the embodiments of FIGS. 1 and 2, housing 11 possesses a "disc" configuration in which the longitudinal and traverse dimensions are substantially equal. The width of the disc is relatively narrow thereby permitting device 10 to be implanted into a patient using a relatively small incision. Sensor 14 is positioned within the flat area of housing 11, which is shown for illustration purposes below the top surface of section 21 but in practice would typically be even therewith. Extension 12 (or 21) could be permanently attached to housing 11 or could be designed to disconnect therefrom so as to be pluggable with section 101 acting as a mating structure between housing 11 and probe section 12. Section 101 can be an adapter having electrical connections therein (not shown) and a snap (or screw) together section for holding probe section 12 in mated relationship with housing 11.

If desired, there could be several different lengths of probe 12 (or probe 12 could be expandable) each to accommodate different size patients. Expansion of probe 12 could be by a screw type turnbuckle, by sections fitting inside sections much like a drapery rod or by such other mating systems as is known in the implantable medical device art. Housing 11 would typically be constructed from solid material, but it could be flexible. In one embodiment, probe section 12 could be flexible to facilitate alignment with the shape or motion of the body and could be relatively thin in both the y and z planes. A flexible probe 12 provides for a comfortable design for the patient. Prior art designs provide for a "one size fits all." However, it is known that all patients are not built the same. Thus, having a flexible probe allows the probe to conform to the shape of the patient's incision site. Also, having a removable probe allows the implanter to choose the proper length of probe 12 based on the patient's size. However, it is important to note that other embodiments might have a permanently attached or non-flexible probe (or any combination of the two). Moreover, the design of device 10 is advantageous, because the design enables device 10 to include more elements to provide a greater amount of functionality (e.g., processing capability, battery recharging, etc.).

In one embodiment, not shown, the width (y) of probe 12 could be narrower even than sensor 14, with sensor 14 supported at the end thereof. Note that several probes 12 could be added to a single housing, each having a sensor placement in close proximity to a potential source of physiological waveforms generated by a human body. The sensors are connected by wires or other suitable conductors, not shown, to the electronics contained in housing 11. Appropriate suture holes 15 can be positioned in device 10, if desired, to facilitate maintaining the device in a proper orientation once implanted. Note that the flat area of housing 11 will prevent device 10 from turning over even if the probe section is tubular, as shown in FIG. 2. A typical distance between sensors 13 and 14 would be 1.6 inches.

FIG. 3 shows a top view of housing 11 having contained therein electronics, such as processor 31, memory 32, battery 33, and transmitter/receiver 35. Processor 31 in combination with suitable executable instructions enables physiological data to be analyzed, stored, processed, and communicated using a number of relatively sophisticated algorithms. Transmitter/receiver 35 enables communication between device 10 and patient communicator 36. Patient communicator 36 thus can be positioned in somewhat close proximity to housing 11

(e.g., within 10 meters) and can be available for receiving data, such as warning signals and/or actual heart rate or other physiological data, from transmitter/receiver 35 via transmitter/receiver 303. In the embodiment shown, recharge circuit 34 has been added in the monitor device 10 to enable battery 33 to be recharged using an external power source. Specifically, charger 301 of patient communicator 36 radiates RF power which is received by recharge circuit 34 of device 10 to recharge battery 33. Also, charger 301 is shown in conjunction an optional warning control 302 to receive signals associated with a low battery condition of battery 33 so as to warn a user to recharge the battery.

The rechargeability of device 10 in combination with other functionality of device 10 enables device 10 to operate in a manner that is fundamentally different than conventional implantable monitoring devices. Specifically, conventional monitoring devices are merely hardware-based circuitry coupled to memory that record physiological data when a defined physical parameter exceeds or falls below some threshold value. The power requirements of such hardware-implemented devices are quite minimal. Thus, there is no benefit of integrating battery recharging functionality in hardware-implemented devices. In contrast, as discussed below, device 10 preferably implements a number of relatively sophisticated algorithms to analyze, process, and communicate physiological data using a microprocessor. To support the processor and software algorithms, a greater amount of power is consumed than conventional hardware-implemented systems. Additionally, for some patients and conditions, it may be appropriate to monitor the patient for up to eighteen months or longer. A battery for supporting the processor and algorithms over this length of time would cause the monitoring device to be of undue size. Alternatively, a smaller battery would likely run out of power and require explanation of the device. Accordingly, some embodiments enable sophisticated monitoring of physiological processes over relatively long periods of time without requiring undue device size and without requiring an explanation procedure to replace the battery of the monitoring device.

The sensor functionality (depicted as sensors 13 and 14 in FIGS. 1 and 2), can be used to capture physiological waveforms. Device 10 optionally processes and records the physiological data. From time to time, on demand, or otherwise, processor 31 utilizes transmitter/receiver 35 to send at least a portion of the recorded signals to external patient communicator 36. The external patient communicator could receive a recording from memory 32 or could receive a real-time reading of the signals obtained from sensors 13, 14. The signals sent to the external device could be the physiological signals directly obtained by sensors 13 and 14 and/or signals processed by processor 31. FIG. 4 shows the same circuitry as FIG. 3, except that recharge coil 41 is located in probe area 12 as opposed to housing 11. In alternative embodiments, other elements (such as processor 31, memory 32, transmitter 35) could be contained within probe area 12.

As previously mentioned, device 10 preferably captures data for a plurality of categories of events and prioritizes among those events. FIG. 5 depicts example table 50 that includes a plurality of "trigger" categories, the priority level of those categories, and the programmable values (if any) for the particular categories that trigger the recordation of physiological data for the corresponding event. Although only single trigger value parameters are shown in FIG. 5, more sophisticated trigger criteria or different triggers may be employed as discussed below. The trigger categories can be established by a clinician individually for a patient and loaded into memory 32 (FIG. 3) under control of processor 31 (FIG. 3) and transmitter/receiver 35 (FIG. 3). Transmitter/receiver 35 could be used for this purpose. Changes (or the initial loading) to table 50 can be made through patient communicator 36 which obtains its information from a local computer as discussed with respect to FIG. 8. Different data or sets of data can be recorded depending upon the various categories depending upon the available sensors, sensor types, and processing algorithms. For each category, the data to be recorded for that category can be established, again using transmitter/receiver 35.

The prioritization of the categories of data can be used for several purposes. In one embodiment, device 10 implements algorithms to facilitate the management of the physiological data in memory 32. For example, device 10 can be implemented to store sets of physiological data in file structures in memory 32. Suitable metadata is associated with the various files to indicate one or several events associated with the physiological data of each file. The metadata could be stored as one or several tag data structures within a header that immediately precedes each set of physiological data. Alternatively, an index structure can be used to identify the event(s) corresponding to each set of physiological data. When the amount of stored physiological data reaches the capacity of memory 32, processor 31 examines the priority levels of the various categories before overwriting any stored data with data associated with a more recent event. Processor 31 preferably overwrites the lowest priority set(s) of physiological data (if overwriting is necessary). If the more recent event is of lower priority than all of the stored sets of physiological data, processor 31 preferably omits storing the data associated with the more recent event.

The metadata identifying the events associated with the sets of physiological data can be used for other purposes. For example, a clinician may communicate a command, using communicator device 36 or otherwise, to obtain data related to a specific category of event. Device 10 processes the command by transmitting each set of physiological data associated with the specific category of event. Thereby, the clinician can obtain the desired data without requiring the device 10 to output all data stored in memory 32. The metadata also is useful in reducing the amount of information needed to store the physiological data. In particular, because the metadata allows multiple events to be associated with each set of physiological data, duplicate recording need not be stored per event as is exhibited by known monitoring devices.

Prioritization schemes can be used for multiple purposes. For example, the stored physiological data is preferably communicated to patient communicator device 36 and subsequently to a clinician in accordance with the priority levels, i.e., highest priority level data is communicated first. In other embodiments, the priority level of an immediately occurring event can be communicated to patient communicated device 36. Depending upon the communicated priority level, patient communicator 36 may provide a different type of warning signal to the patient. If the priority level is relatively low, the signal can merely indicate to the patient that the patient should allow the physiological data to be communicated to a clinician within the near future. Alternatively, if the priority level is relatively high, the signal can indicate to the patient that the patient should seek immediate medical attention. Depending upon the intended application of the device, the prioritization scheme for warning the patient can be implemented independently of the prioritization scheme associated with the memory management of device 10.

In some embodiments, reference signatures are applied to the analysis of physiological waveforms. In essence, the reference signatures enable physicians to define waveform characteristics to which pattern matching analysis is applied against the physiological waveform of the patient. The reference signatures preferably define multiple point reference targets (e.g., 4-6) with tolerable variations (e.g., 15-30%). If the measured physiological waveform deviates from the reference targets beyond the tolerable variations, a trigger is generated and data recordation occurs.

For example, the physiological waveform for ECG signals includes a "P wave," a "QRS complex," and a "T wave." The signal processing of monitor device 10 preferably identifies each segment and determines the relevant characteristics of the segments (e.g., the segment lengths, segment amplitude, polarization, etc.). The reference signature can define amplitude parameters, timing parameters, or other suitable parameters for one or several of these relevant characteristics. Also, the timing parameters of a reference signal can involve the timing of the individual segments and/or the timing relationships between the segments. By providing such functionality, a physician can more accurately define a monitoring regimen adapted for a particular patient. Additionally, static conventional trigger criteria can be used in combination with the reference signatures in some embodiments.

In addition to performing memory management according to a prioritization scheme, device 10 preferably selectively stores data in memory 32 according to known locations of memory defects in memory 32. FIG. 6 depicts flowchart 60 for analyzing memory 32 for memory defects. In step 601, a memory check procedure is initiated. In step 602, known data is written to all (or selected) memory locations. The current consumed by each write transaction is monitored (step 604) to detect defective memory locations. Also, data is read out of the memory locations and compared against the expected values (at step 603) to check for defective locations. Logical comparisons are made at steps 605 and 606 to respectively determine if the consumed current associated with the memory locations is within acceptable limits and whether appropriate value was retrieved from the memory locations. Depending upon the logical comparisons, faulty memory locations are recorded (step 607) or no action is performed.

FIG. 7 depicts a flowchart for processing, storing, and communicating physiological data by a monitoring device and, optionally, a patient communicator according to one representative embodiment. In step 701, physiological data is received from suitable circuitry of device 10 (e.g., as measured by sensors 13 and 14, converted to digital form, filtered or otherwise processed, and/or the like). The data is preferably maintained in an on-going manner in a temporal window. Analysis of the data in the window or a subset thereof occurs to determine whether an event of interest has occurred (step 702). If not, the process of receiving data and analyzing the data continues. If one or several events are detected in the received data, additional data is received for recordation after the identified beginning of the event(s) (step 703). The data recording continues for a predetermined period of time or until an appropriate criteria is satisfied (e.g., the physiological condition returns to a "normal" state). The amount of data captured for a particular event can be implemented as a programmable variable that is set using communication with patient communicator device 36. A different amount of data could be captured for each event as deemed appropriate by the patient's physician.

In step 704, the relevant data is stored in memory 32 of monitoring device 10. The data is preferably stored subject to the prior detection of defective memory locations. Additionally, if the memory capacity has been reached, the data storage preferably occurs according to event prioritization. In some embodiments, a compression scheme is applied to the physiological data stored in memory 32 of monitoring device 10. Although the data storage is depicted after the receipt of data in the flowchart, it shall be appreciated that, when the flowchart is implemented in software, the data storage occurs concurrently with the receipt of data. In step 705, the stored data is tagged with suitable metadata to identify the event(s) associated with the data.

In step 706, an attempt is made to establish a wireless communication connection with patient communicator device 36 using a suitable wireless communication protocol. If a communication connection is established, the monitoring device communicates a signal to the patient communicator that one or several events of interest have occurred. In step 707, the patient communicator provides a suitable signal or alarm to alert the patient. The external alarm could be audible to the patient, a mechanical vibration, a flashing light, a display of text with instructions for the patient, or any suitable combination of thereof.

Additionally, in step 708, monitoring device 10 communicates the physiological data to the patient communicator device for storage therein. The communicated physiological data can be deleted from memory 32 upon successful communication to the patient communicator device. Alternatively, the physiological data can be temporarily retained in memory and subsequently deleted when memory capacity is needed for other data. In some embodiments, the physiological data is transferred from monitoring device 10 to patient communicator device 36 in a compressed format. The data is preferably subsequently decompressed by a software module of a computer when patient communicator device 36 is coupled to the computer.

The decompressed physiological data is formatted in a suitable manner by the software module on the computer (step 709). The physiological data can be formatted as time-samples of the physiological waveform. In one embodiment, an image or video file is created that graphically depicts multiple cycles of the ECG waveform of the patient (in addition to or in lieu of the raw digital samples). Additional information is preferably included within the image(s). For example, patient identification information can be included therein. Additionally, portions of the ECG waveform exhibiting aberrant characteristics can be automatically identified (e.g., rendered using a color different from the color used to render other parts of the waveform). The particular trigger event(s) associated with the physiological data can be identified in the image(s). In step 710, the formatted physiological data is communicated to a suitable clinician. In one embodiment, the created file is attached to an e-mail and communicated to an identified e-mail address. The e-mail can contain suitable information (e.g., patient identification, trigger event(s), time of occurrence, etc.). In alternative embodiments, formatting of the file(s) can be performed by the patient communicator device. For example, the patient communicator device can store the formatted images file in its memory and the stored files can be retrieved by a computer via the USB interface using conventional file operations.

The described communication of physiological data to and from a clinician occurs in a substantially more efficient manner than known monitoring devices. Specifically, known monitoring devices communicate physiological data over a phone line to a specialized service via a modem. The process for communicating physiological data by known monitoring devices is cumbersome for the patient and also unduly time consuming for the clinician. In contrast, some representative embodiments place a relatively light burden on the patient (i.e., the patient need only connect the patient communicator to an Internet-enabled computer). Moreover, the clinician may access the physiological data in an efficient manner and analyze data in a convenient format.

FIG. 8 depicts one embodiment for communication of data from patient communicator device 10 to doctor 86. As shown in FIG. 8, USB port 81 on patient communicator 36 could be connected to USB port 83 on computer 84 via cable 82. Although any other suitable connection may be employed, USB ports are preferred due to their wide availability on personal computers, ease of use, and the ability to allow patient communicator device 36 to recharge its battery during the connection to computer 84. This embodiment is particularly advantageous, because the patient communicator device 36 can be used to perform a number of tasks for the patient (data retrieval, data communication to a clinician, and recharging of device 10) in an efficient manner for the patient. Upon receipt of data, computer 84 formats that data into an e-mail for communication with a remote location, such as doctor's office 803. This remote communication occurs via network 802 which, in one embodiment, can be the Internet. Doctor 86, using computer 85 and perhaps memory 86, can send an e-mail back to the patient's computer 84. The data contained in this return e-mail can then be transmitted to the patient's implanted device 10 via patient communicator 36. The data in the return e-mail can, for example, change the settings and/or one or more trigger values in the imbedded device or the data could instruct the device to report or monitor different data.

According to one embodiment, FIG. 9 depicts flowchart 900 for controlling how a caregiver, such as Doctor 86 (FIG. 8), working from computer 85, can receive information from one or more patients and send information back to the patients using e-mail or suitable messaging. The delivery of e-mails is checked in step 901. This can be automatic or can be user controlled.

If one or several new e-mails are identified (step 902), the corresponding data contained therein is read (step 903). A logical comparison is made upon whether the new data should be processed by an analysis routine (step 904). The system could be configured so that all incoming data is analyzed or only data satisfying certain criteria is reviewed. In step 905, the received data is analyzed. During the analysis, the received data is compared to the previously received data received to identify a possible relevant trend in the patient (e.g., deterioration of the patient's condition). Any number of other analysis algorithms could be employed at this step. In addition to autonomous analysis by computer-implemented algorithms, physician or other clinician review of the data can be performed at this step.

In step 906, based partially (or entirely) on the results of step 905 and partially (or entirely) under control of the caregiver, a change to a trigger value, a priority code, or other value (or any other changes to the implanted patient device) is made. This "revision" data is packaged as part of an e-mail (either imbedded therein or as an attachment) and the e-mail is sent to the patient's computer (step 907). Once received by the patient's computer, the patient communicator device 36 extracts the data from the e-mail and subsequently communicates the revision data to monitoring device 10. Monitoring device 10 modifies its operations according to the revision data.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An implantable device for recording physiological waveforms, the device comprising:

electronic circuitry for sampling a physiological waveform of a patient;

memory for storing physiological data;

a processor under the control of executable instructions for processing samples of the physiological waveform, wherein the processor is programmed (i) to detect a predefined event in the physiological waveform by analyzing the physiological waveform against multiple parameters with each of the multiple parameters applied to a different segment of the physiological waveform and (ii) to store physiological data in the memory in response to detection of the predefined event, wherein the processor executes a diagnostic routine to identify locations in the memory that consume an amount of current above a threshold value during write memory transactions and the processor avoids storing the physiological data in the identified locations; and a wireless communication module for communicating with a device external to the patient after the implantable device has been implanted in the patient.

2. The implantable device of claim 1 wherein the processor analyzes the physiological waveform for a plurality of events.

3. The implantable device of claim 2 wherein prioritization levels for the plurality of events are stored in memory of the implantable device.

4. The implantable device of claim 3 wherein the processor overwrites previously stored physiological data with newly acquired physiological data according to the prioritization levels, when stored physiological data reaches a memory capacity of the implantable device.

5. The implantable device of claim 3 wherein the prioritization levels are programmable by the device external to the patient.

6. The implantable device of claim 1 wherein the processor associates identifiers of detected events with physiological data in the memory.

7. The implantable device of claim 1 wherein the processor processes a command from the device external to the patient to communicate only physiological data associated with an identified event or events.

8. The implantable device of claim 1 wherein the processor executes a self-diagnostic routine to identify locations in the memory that are non-functional.

9. The implantable device of claim 1 wherein physiological data is communicated by the processor via the communication module to the device external to the patient in a compressed format.

10. The implantable device of claim 1 wherein the processor applies different sets of multiple parameters to the physiological waveform in a time-dependent manner.

11. The implantable device of claim 10 wherein at least one set of the multiple parameters is applied to the physiological waveform during times of expected lower-activity levels of the patient and another set of the multiple parameters is applied to the physiological waveform during times of expected higher-activity levels of the patient.

12. The implantable device of claim 1 wherein each of the multiple parameters define a respective amplitude value.

13. The implantable device of claim 12 wherein the processor further applies a respective tolerance value for variation of the physiological waveform from each of the amplitude values.

14. The implantable device of claim 1 wherein the processor communicates a signal to the device external to the patient to indicate that the predefined event has occurred.

* * * * *